United States Patent
Koftis et al.

(10) Patent No.: US 11,198,671 B2
(45) Date of Patent: Dec. 14, 2021

(54) ONE-POT ORGANO-PSEUDOCATALYTIC C—H ACTIVATION APPROACH FOR THE PREPARATION OF VORTIOXETINE AND VORTIOXETINE INTERMEDIATE

(71) Applicant: VIO AG PHARMACEUTICALS S.A., Athens (GR)

(72) Inventors: Theocharis V. Koftis, Salonika (GR); Efstratios Neokosmidis, Salonika (GR); Thanos Andreou, Salonika (GR); Petros Gkizis, Salonika (GR); Alexandra Lithadioti, Salonika (GR)

(73) Assignee: VIO AG PHARMACEUTICALS S.A., Kifisia (GR)

( * ) Notice: Subject to any disclaimer, the term of this patent is extended or adjusted under 35 U.S.C. 154(b) by 0 days.

(21) Appl. No.: 17/251,808

(22) PCT Filed: Jun. 19, 2019

(86) PCT No.: PCT/EP2019/025189
§ 371 (c)(1),
(2) Date: Dec. 13, 2020

(87) PCT Pub. No.: WO2019/242889
PCT Pub. Date: Dec. 26, 2019

(65) Prior Publication Data
US 2021/0163407 A1 Jun. 3, 2021

(30) Foreign Application Priority Data

Jun. 20, 2018 (WO) ................. PCT/EP2018/025164
Jun. 19, 2019 (WO) ................. PCT/EP2019/025189

(51) Int. Cl.
*C07C 319/14* (2006.01)
*C07C 323/37* (2006.01)

(52) U.S. Cl.
CPC .......... *C07C 319/14* (2013.01); *C07C 323/37* (2013.01)

(58) Field of Classification Search
CPC . C07D 295/096; C07C 319/14; C07C 323/37; C07F 13/005
See application file for complete search history.

(56) References Cited

U.S. PATENT DOCUMENTS 10,227,317 B2 * 3/2019 Singh ................. C07D 295/096
10,836,730 B2 * 11/2020 Sathe ................. C07D 241/04

FOREIGN PATENT DOCUMENTS

| IN | 6843CHE2015 | A1 | 6/2017 | |
| IN | 201641001393 | A2 | 7/2017 | |
| WO | 2015/155153 | A1 | 10/2015 | |
| WO | WO-2015155153 | A1 * | 10/2015 | ......... C07D 295/096 |

OTHER PUBLICATIONS

X. Huang et al., 31 Synthetic Communications, 2823-2828 (2001) (Year: 2001).*
L. Wang et al., 31 Synthetic Communications, 1227-1232 (2001) (Year: 2001).*
J. Malmgren et al., 19 Chemistry A European Journal, 10334-10342 (2013) (Year: 2013).*
L. Wen et al., 82 Journal of Organic Chemistry, 1428-1436 (2017) (Year: 2017).*
H. Niu et al., 9 Organic and Biomolecular Chemistry, 5039-5042 (2011) (Year: 2011).*
A. Wagner et al., 79 Journal of Organic Chemistry, 2263-2267 (2014) (Year: 2014).*
S. Zisopoulou et al., 52 Synthesis, 2662-2666 (2020) (Year: 2020).*
A. Yoshimura et al., 116 Chemical Reviews, 3328-3435 (2016) (Year: 2016).*
D. Merritt et al., 48 Angewandte Chemie, International Edition, 9052-9070 (2009) (Year: 2009).*
M. Wang et al., 13 Chemistry An Asian Journal, 2195-2207 (2018) (Year: 2018).*
A. Krief et al., Synlett, 484-486 (2006) (Year: 2006).*
Li Wang et al: "Hypervalent Iodine in Synthesis 55: An Efficient Method for Synthesis of Aryl Sulfides by Palladium-Catalyzed Reaction of Hypervalent Iodonium Salts With Mercaptans" Synthetic Communications, vol. 31, No. 8, Jan. 1, 2001, p. 1227-1232.
Joel Malmgren et al: Arylation with Unsymmetrical Diaryliodonium Salts:A chemosensitive Study, Chemistry-A European Journal,vol. 19, No. 31, Jun. 20, 2013, p. 10334-10342.
Li-Rong Wen et al: "Synthesis of 1-Thio-Substituted Isoquinoline Derivatives by Tandem Cyclization of Isothiocyanates". Journal of Organic Chemistry, vol. 82, No. 3, Jan. 23, 2017, p. 1428-1436.
Hong-Ying Niu et al: "CuBr Catalyzed C_N cross coupling reaction of purines and diaryliodonium salts to 9-arylpurines" Organic and Biomolecular Chemistry, vol. 9, No. 14, Jan. 1, 2011, p. 5039-5042.

* cited by examiner

*Primary Examiner* — Alexander R Pagano
(74) *Attorney, Agent, or Firm* — AKC Patents, LLC; Aliki K. Collins

(57) ABSTRACT

The present invention relates to a novel process for the preparation of Vortioxetine and a key intermediate thereof by employing a novel one-pot organo-pseudocatalytic C—H activation approach via hypervalent iodine chemistry.

7 Claims, No Drawings

ONE-POT ORGANO-PSEUDOCATALYTIC C—H ACTIVATION APPROACH FOR THE PREPARATION OF VORTIOXETINE AND VORTIOXETINE INTERMEDIATE

TECHNICAL FIELD OF THE INVENTION

The present invention relates to a novel process for the preparation of a compound useful as an intermediate in the preparation of the active pharmaceutical ingredient Vortioxetine.

BACKGROUND OF THE INVENTION

Vortioxetine is a drug used for the treatment of depression and anxiety, developed by Lundbeck. It is marketed as Brintellix in Europe and as Trintellix in the USA. Vortioxetine is disclosed in example 1e of WO 2003/029232 A1.

There are a number of methods disclosed in the prior art for the preparation of Vortioxetine.

In WO2013102573, Vortioxetine is prepared according to Scheme 1, by reaction of a mixture of 2-bromothiophenol, 1-iodo-2,4-dimethylbenzene and piperazine, in the presence of a Pd catalyst.

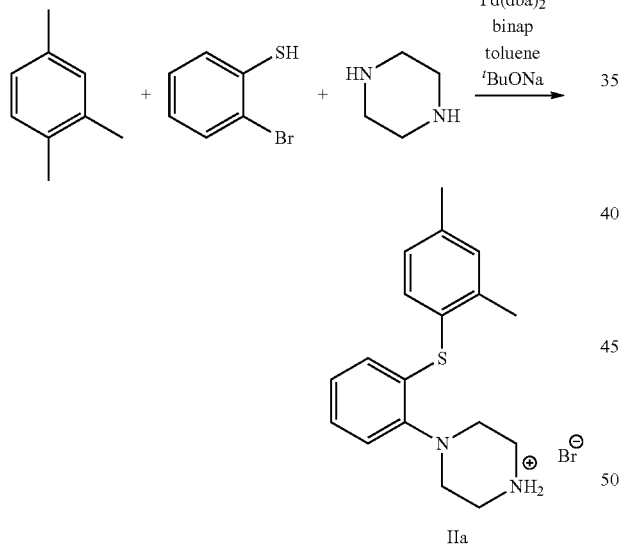

Scheme 1

In WO2014161976, a different synthetic approach is provided, wherein an alternative way of assembling the two aromatic components is realized. This is a three-step process, compared to the one disclosed in scheme 1, however the use of expensive o-bromothiophenol and Pd catalyst is avoided. The precursor of intermediate compound of formula I, i.e. the respective nitro-derivative, is formed by means of alkylation of 2,4-dimethylthiophenol with o-nitrochlorobenzene. Fe catalysis for reducing the nitro group to the desired aromatic amine is required, to provide the key-intermediate of compound of formula I. Vortioxetine is then provided upon double alkylation of the free aromatic amine group.

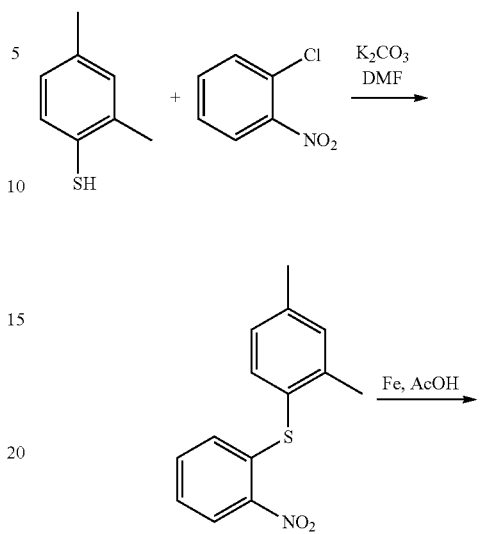

Scheme 2

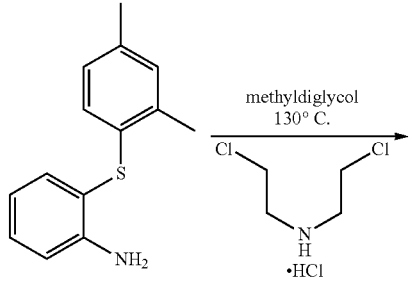

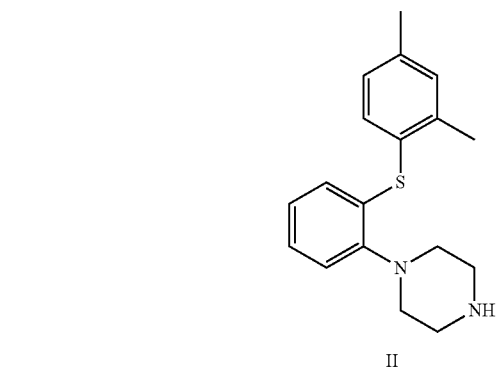

It would be desirable to improve the synthetic procedures available in the prior art for the preparation of Vortioxetine, particularly maintain simple and cost-effective reagents while making the overall synthetic process shorter.

SUMMARY OF THE INVENTION

The invention provides a novel process for the preparation of compound of formula I by utilizing a one-pot organo-pseudocatalytic reaction approach based on hypervalent iodine chemistry. Compound of formula I is an intermediate useful for the synthesis of Vortioxetine (compound of formula II).

Scheme 3

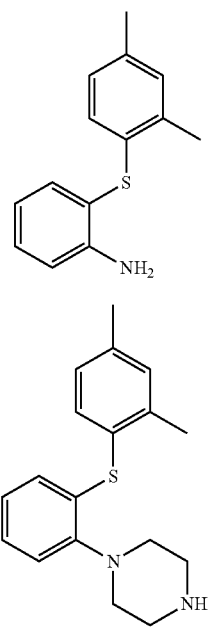

The invention further provides an improved process for the preparation of Vortioxetine, comprising preparation of compound of formula I according to the novel process of the present invention and conversion of compound of formula I to Vortioxetine compound of formula II.

Definitions

"Acid" refers to any compound that contains hydrogen and dissociates in water or solvent to produce positive hydrogen ions, as well as Lewis acids, including but not limited to acids such as hydrochloric acid, hydrobromic acid, sulfuric acid, nitric acid, phosphoric acid, acetic acid, trihaloacetic acid (e.g., trifluoroacetic acid), hydrogen bromide, maleic acid, sulfonic acids such as methanesulfonic acids, toluenesulfonic acids and camphorsulfonic acids, propionic acids such as (R)-chloropropionic acid, phthalamic acids such as N—[(R)-1-(1-naphthyl) ethyl]phthalamic acid, mandelic acid, tartaric acids such as D- or L-tartaric acid, and dibenzyl-L-tartaric acid and its derivatives, such as diaroyl tartaric acids, lactic acids, camphoric acids, aspartic acids, citronellic acids, and so forth. Thus, the term includes weak acids such as ethanoic acid and hydrogen sulfide; strong organic acids such as methanesulfonic acid, trifluoroacetic acid, and so forth.

"Base" when used herein includes hydroxides or alkoxides, hydrides, or compounds such as amine and its derivatives, that accept protons in water or solvent. Thus, exemplary bases include, but are not limited to, alkali metal hydroxides and alkoxides (i.e., MOR, wherein M is an alkali metal such as potassium, lithium, or sodium, and R is hydrogen or alkyl, as defined above, more preferably where R is straight or branched chain C1-5 alkyl, thus including, without limitation, potassium hydroxide, potassium tert-butoxide, potassium tert-pentoxide, sodium hydroxide, sodium tert-butoxide, lithium hydroxide, etc.); other hydroxides such as magnesium hydroxide (Mg(OH)2) or calcium hydroxide (Ca(OH)2), barium hydroxide (Ba(OH)2); alkali metal hydrides (i.e., MH, wherein M is as defined above, thus including, without limitation, sodium, potassium, and lithium hydrides); alkylated disilazides, such as, for example, potassium hexamethyldisilazide and lithium hexamethyldisilazide; carbonates such as potassium carbonate (K2CO3), sodium carbonate (Na2CO3), potassium bicarbonate (KHCO3), and sodium bicarbonate (NaHCO3), alkyl ammonium hydroxides such as tetrabutyl ammonium hydroxide (TBAH) and so forth. Aqueous bases include metal hydroxides, for example, hydroxides of Group 1/Group 2 metals such as Li, Na, K, Mg, Ca, etc. (e.g., aqueous LiOH, NaOH, KOH, etc.), alkyl ammonium hydroxides, and aqueous carbonates. Non-aqueous bases include but not limited to, amines and their derivatives, for example, trialkyl amine (e.g., Et3N, diisopropylethyl amine, etc.), and aromatic amine (e.g., Ph-NH2, PhN(Me)H, etc.); alkali metal alkoxides; alkali metal hydrides; alkylated disilazides; and non-aqueous carbonates.

DETAILED DESCRIPTION OF THE INVENTION

In a first embodiment, the present invention provides a process for the preparation of compound of formula I, comprising subjecting compound of formula III, wherein R is hydrogen or o-aminothiophenolic radical, into reaction with compound of formula IV (Scheme 4). Anion X originates from the preparation of the aryl iodonium salt (IV), usually from the acid employed in its preparation, so it is a conjugate base. There are a plurality of methods known in the prior art available for the preparation of those compounds (see below) and anion X may be selected among a large number of conjugated bases related to said acids. In addition, it may be the case that the initial aryliodonium salt prepared is subjected to anion exchange in the presence of another ionic compound. Accordingly, anion X may represent a relatively big diversity of anions. Preferably, anion X may be halogen, tosylate, boron tetrafluoride, triflate, perchlorate, trifluoroacetic or acetic anion.

The inventors have surprisingly found that o-disubstituted diaryliodonium salts (IV) react with compounds of formula III, which may be either thiophenols (R=H, compounds of formula IIIa) or disulfides (R= o-aminothiophenolic radical, compounds of formula IIIb) to provide compound of formula I (Scheme 4). The reaction provides access to compound of formula I from readily available and cost-effective starting materials, thus avoiding the requirement of reducing the nitro group to amine, as disclosed in the prior art. At the same time, the direct attachment of an amine-bearing moiety to the dimethylaryl substrate is achieved, without the need to use expensive metal catalysts, such as Pd, which is taught in prior art.

Scheme 4

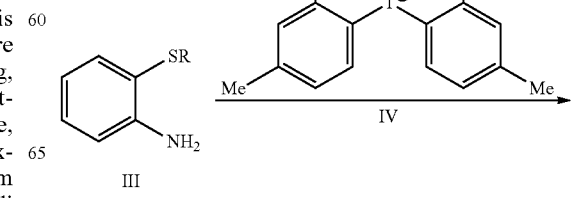

-continued

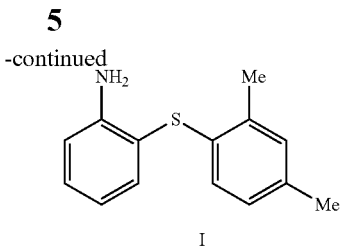
I

Scheme 5

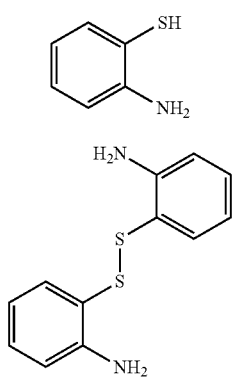

A byproduct of the reaction between compound of formulae III and IV (not shown) is the remaining moiety of the aryliodonium salt, i.e. 1-iodo-2,4-dimethylbenzene (compound of formula V). This byproduct may advantageously be isolated according to the present invention and used to prepare a new compound of formula IV, which according to prior art is a well-established procedure [Bielawksi et al, Chemistry Open 2014, 3 (1), pp 19-22 and Monastyrskyi et al, J. Org. Chem. 2015, 80 (5), pp 2513-2520]. Such a feature renders the whole process pseudocatalytic with respect to the expensive iodine-containing reagent (compound of formula IV).

Diaryliodonium salts of general formula IV may be prepared according to well established prior art procedures. A comprehensive review by Merritt A., Olofsson B., "*Diaryliodonium salts: A journey from Obscurity to Fame*", Ang. Chemie Int. Ed. 2009, 48, 9052, describes among other topics, various existing preparation methods of such compounds. The contents of the cited document are incorporated herein by reference. Diaryliodonium salts may be prepared according to two major approaches, via preformed hypervalent iodine reagents or by one-pot syntheses wherein iodine requires oxidation. An important feature of the latter, is the requirement of an oxidizing reagent. m-chloroperbenzoic acid is a common choice, however more recent publications try to employ more environmentally friendly reagents, such as urea-hydrogen peroxide (Merritt, E.; Malmgren, J; Klinke, F; Olofsson, B; "*Synthesis of Diaryliodonium Triflates Using Enviromentally Bening Oxidizing Agents*", Synlett 2009, 14, 2277). Other promising oxidizing agents may well be envisaged in this context, as for example TRIAZOX.

The reaction between compound of formula III and compound of formula IV is a reaction belonging to the aryliodonium salts' chemistry. It may be performed in the presence of a base and/or a suitable additive. As a general principle, the base and/or any other suitable additive enhances the nucleophilic character of the sulfur atom. Therefore, the choice of the base and/or additive depends among other factors on the nature of the substrate (IIIa or IIIb). According to prior art procedures (Krief et al, Synlett 2006, 3, p. 484) a strong base, such as sodium hydride, may be used to deprotonate the thiol moiety. Other prior art disclosures combine the use of less strong base, such as sodium bicarbonate, with tetrakis(triphenylphosphine)palladium to prepare aryl sulfides by reacting hypervalent iodonium salts with mercaptans (Wang et al, Synthetic Communications 2001, 31(8), 1227). In this context, the present invention has employed a variety of bases to perform the reaction. Notably, bases have proved to be effective in the case of the disulfide substrate IIIb, as well. It has additionally been reported that Zinc and Aluminium Chloride, can also be employed in the case of IIIb, as well (Movassagh et al, Phosphorus, Sulfur, Silicon, 2005, 180, 2275). The choice of the base and/or suitable additive is not important in the context of the present invention and can be realized by a skilled person's common general knowledge.

The reaction medium may be selected from polar aprotic solvents, non polar solvents and deep eutectic solvents (DES). DESs are systems formed from a eutectic mixture of Lewis or Brønsted acids and bases which can contain a variety of anionic and/or cationic species. They are considered more eco-friendly and pose useful characteristics such as low vapor pressure and the possibility of recycling. A comprehensive review of DES solvents can be found in Chem. Rev. 2014, 114, 11060 by Smith et al.

In still another preferred embodiment, R is hydrogen and compound of formula III is compound of formula IIIa.

In still another preferred embodiment, R is o-aminothiophenolic radical and compound of formula III is compound of formula IIIb.

In still another preferred embodiment, the above described process, comprising the reaction between compound of formulae III and IV, further comprises isolating the resulting byproduct (compound of formula V). Compound of formula V may then be recycled to provide compound of formula IV again.

In a second embodiment, the present invention provides a process for the preparation of compound of formula II, comprising the following steps:
  a) subjecting compound of formula III, wherein R is hydrogen or o-aminothiophenolic radical into reaction with compound of formula IV;

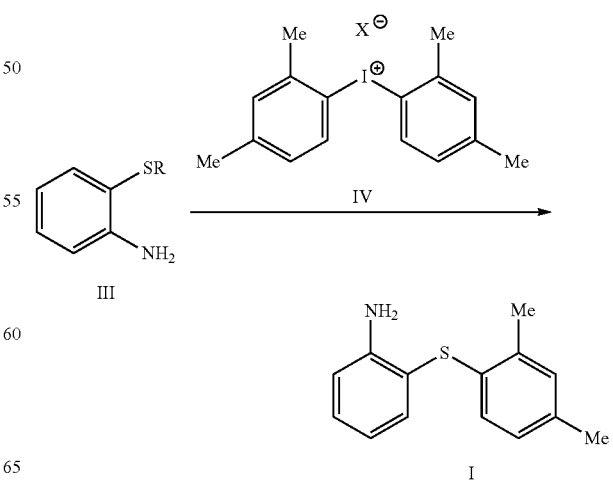

b) converting compound of formula I into compound of formula II,

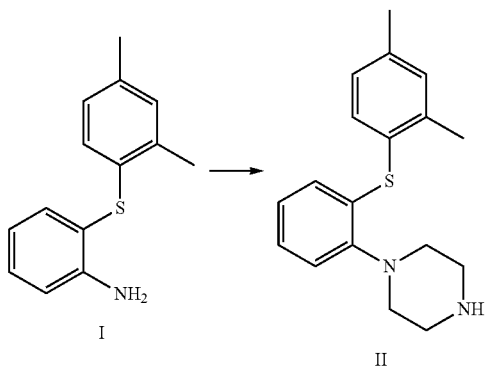

I

II wherein X is an anion as defined in the first embodiment.

Conversion of compound of formula I into compound of formula II may be realized according to procedures disclosed in the prior art. The conversion may also be achieved according to a skilled person's general knowledge.

In WO2014161976 compound of formula I is converted to compound of formula II by reacting compound of formula I with 2,2'-dichlorodiethylamine. In addition, 2,2'-dibromodiethylamine or 2,2'-iminodiethanol dimethanesulfonate may be used instead.

In WO2015155153 compound of formula I is first converted to its respective iodine, by replacing the aromatic amine with iodine and this intermediate is reacted with CuI and piperazine in the presence of a ligand to provide compound of formula II.

In WO2016125191 compound of formula I is first converted to a double alkylated amine intermediate (compound of formula N), which is then converted to its respective ring-closed derivative (compound of formula M) and if required deprotection of the amine group provides compound of formula II.

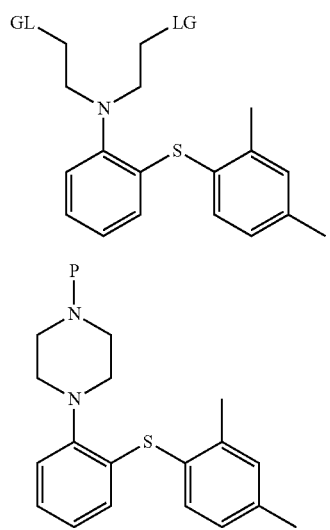

N

M

In EP3023417, compound of formula I is converted to a bis-substituted intermediate (compound of formula L, R is aldehyde or carboxy group) which is subsequently reacted with a compound of formula Q (Z being H or amino protecting group) to provide the respective derivative with the piperazine ring and if required deprotection of the amine group towards compound of formula II.

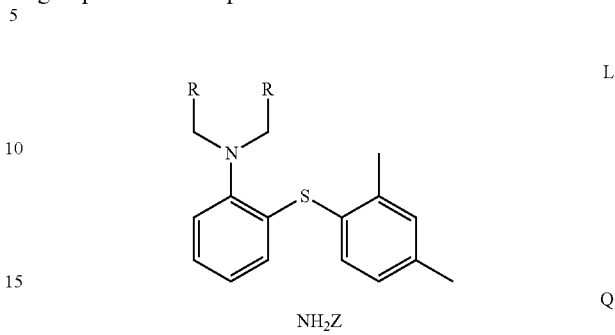

L

Q

In CN104230852 compound of formula I is reacted with N,N-bis(2-chloroethyl)-4-methyl-benzenesulfonamide and the resulting intermediate compound is deprotected from the p-toluolylsulfonyl moiety to provide compound of formula II.

In CN104829557 compound of formula I is converted to compound of formula R by reacting compound of formula I with 2-chloro-acetyl chloride, followed by reaction with 2-amino-ethanol and cyclization. Intermediate compound of formula R is converted to compound of formula II under reductive conditions.

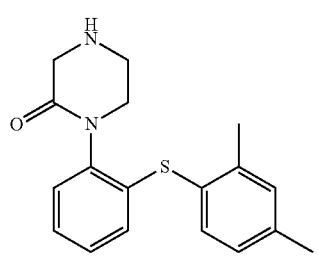

R

Accordingly, a skilled person may convert compound of formula I into compound of formula II by using any of the methods described above.

In a preferred embodiment, step b is performed by reacting compound of formula I with 2,2'-dichlorodiethylamine, and 2,2'-dibromodiethylamine and 2,2'-iminodiethanol dimethanesulfonate.

In still another preferred embodiment, compound of formula III is compound of formula IIIa.

In still another preferred embodiment, compound of formula III is compound of formula IIIb.

In a further embodiment the present invention provides a use of compound of formula IV in a process for the preparation of compound of formula I.

In another embodiment the present invention provides a use of compound of formula III in a process for the preparation of compound of formula I.

In still another embodiment the present invention provides a use of compound of formula IV in a process for the preparation of compound of formula II.

In another embodiment the present invention provides a use of compound of formula III in a process for the preparation of compound of formula II.

In a further embodiment the present invention provides a process for the preparation of compound of formula II comprising the step of reacting compound of formula III with compound of formula IV to provide compound of formula I.

EXAMPLES

Example 1: Synthesis of Aryl Iodonium Salt IV

Example 1a

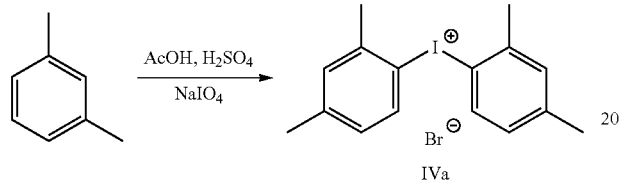

IVa m-xylene (52 mmol, 6.4 ml) was dissolved in 10 ml sulfuric acid and 70 ml glacial acetic acid and the resulting mixture was warmed up, with stirring, to 50-55° C. While keeping the same temperature, sodium periodate (4.28 g, 20 mmol) was slowly added portionwise over 1.5 h. Stirring was continued, warmed at the same temperature for 1.5 h. The cooled final mixtures were poured into stirred ice-water (200 g). The resulting solid was filtered off. The cold filtrates were extracted with diethyl ether (4×100 ml) and the ethereal extracts were discarded. A solution of potassium bromide (4.0 g, 33.6 mmol) in water (20 mL) was added to the vigorously stirred remaining aqueous solution. After 1 h, the precipitated diaryliodonium bromide (IVa) was collected by filtration and the crystals were washed well with cold water until the filtrates were neutral, dried into vacuum desiccators to give 5.3 g of crude product (IVa).

$^1$H NMR (500 MHz, CDCl$_3$) δ 7.87-7.85 (d, J=8.2 Hz, 2H), 7.09 (s, 2H), 6.89-6.87 (d, J=8.2 Hz, 2H), 2.58 (s, 6H), 2.26 (s, 6H).

$^{13}$C NMR (126 MHz, CDCl$_3$) δ 142.16, 140.08, 136.43, 132.22, 129.53, 121.69, 25.49, 21.15

Example 1b

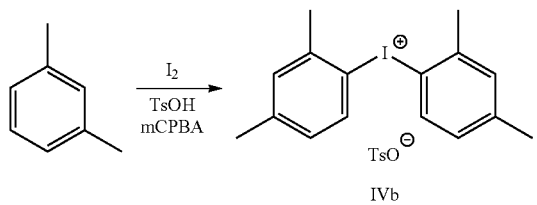

IVb

Iodine (2.98 g, 11.8 mmol), m-xylene (5.81 ml, 47.2 mmol) and m-chloroperoxybenzoic acid (6.12 g, 35.4 mmol) are added in 115.5 dichloromethane. p-toluenesulfonic acid monohydrate (8.968 g, 47.2 mmol) are added and the resulting mixture is stirred under reflux conditions for 14 hours. When TLC analysis shows consumption of starting material, heating is interrupted and reaction mixture is concentrated under vacuum. The residue is then chromatographed over silica gel to yield compound IVb as a yellow solid (mp 159-160° C.).

Synthesis of Aryl Iodonium Salt IV from Recovered 1-iodo-2,4-dimethyl-benzene 1-iodo-2,4-dimethyl-benzene is used to prepare anew the aryl iodonium salt (compound of formula IV) according to prior art procedures disclosed in Bielawksi et al, Chemistry Open 2014, 3 (1), pp 19-22 and Monastyrskyi et al, J. Org. Chem. 2015, 80 (5), pp 2513-2520.

Example 2: Synthesis of Compound of Formula I from Aminothiophenol IIIa

Example 2a

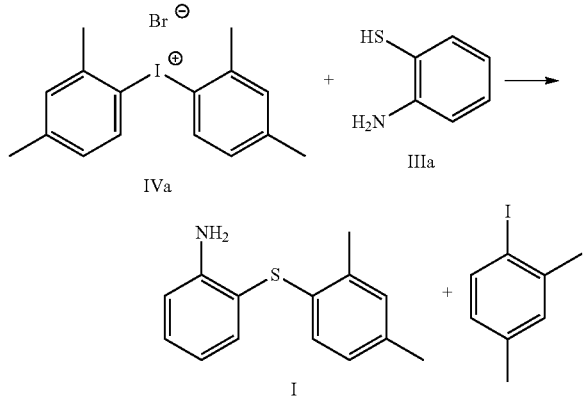

Diaryliodonium salt IVa (150 mg, 0.36 mmol) and sodium hydride 60% dispersion in mineral oil (29 mg, 0.72 mmol) are added in an autoclave. Then aminothiophenol IIIa (0.077 ml, 0.72 mmol) is added, along with 2.5 ml tetrahydrofuran. The mixture is stirred till reaction is completed.

DM water is added and the resulting mixture is extracted with dichloromethane twice. Combined organic layers are dried over sodium sulfate. Solvents are distilled off and the residue is chromatographed over silica gel to afford 47 mg of compound of formula I (57% yield). 1-iodo-2,4-dimethylbenzene was also isolated in quantitative yield (88 mg).

Example 2b

Diaryliodonium salt IVa (150 mg, 0.36 mmol) and sodium hydride 60% dispersion in mineral oil (29 mg, 0.72 mmol) are added in a round-bottomed flask. Then aminothiophenol IIIa (0.077 ml, 0.72 mmol) is added, along with 2.5 ml dimethylsulfoxide. The mixture is stirred till reaction is completed.

DM water is added and the resulting mixture is extracted with dichloromethane twice. Combined organic layers are dried over sodium sulfate. Solvents are distilled off and the residue is chromatographed over silica gel to afford 41 mg of compound of formula I (50% yield). 1-iodo-2,4-dimethylbenzene was also isolated in 86% yield (72 mg).

Example 2c

Diaryliodonium salt IVa (150 mg, 0.36 mmol) and sodium hydride 60% dispersion in mineral oil (29 mg, 0.72 mmol)

are added in a round-bottomed flask. Then aminothiophenol IIIa (0.077 ml, 0.72 mmol) is added, along with 2.5 ml toluene. The mixture is stirred till reaction is completed.

DM water is added and the resulting mixture is extracted with dichloromethane twice. Combined organic layers are dried over sodium sulfate. Solvents are distilled off and the residue is chromatographed over silica gel to afford 39 mg of compound of formula I (47% yield). 1-iodo-2,4-dimethylbenzene was also isolated in quantitative yield (88 mg).

Example 2d

Diaryliodonium salt IVa (0.15 g, 0.36 mmol) and sodium methoxide (39 mg, 0.72 mmol) are added in a round-bottomed flask. Then aminothiophenol IIIa (0.077 ml, 0.72 mmol) is added, along with 2.5 ml toluene. The mixture is stirred till reaction is completed.

DM water is added and the resulting mixture is extracted with dichloromethane twice. Combined organic layers are dried over sodium sulfate. Solvents are distilled off and the residue is chromatographed over silica gel to afford 39 mg of compound of formula I (47% yield). 1-iodo-2,4-dimethylbenzene was also isolated in 92% yield (76 mg).

Example 2e

Diaryliodonium salt IVa (0.15 g, 0.36 mmol) and sodium methoxide (39 mg, 0.72 mmol) are added in a round-bottomed flask. Then aminothiophenol IIIa (0.077 ml, 0.72 mmol) is added, along with 2.5 ml methanol. The mixture is stirred till reaction is completed.

DM water is added and the resulting mixture is extracted with dichloromethane twice. Combined organic layers are dried over sodium sulfate. Solvents are distilled off and the residue is chromatographed over silica gel to afford 21 mg of compound of formula I (25% yield). 1-iodo-2,4-dimethylbenzene was also isolated in 56% yield (47 mg).

Example 2f

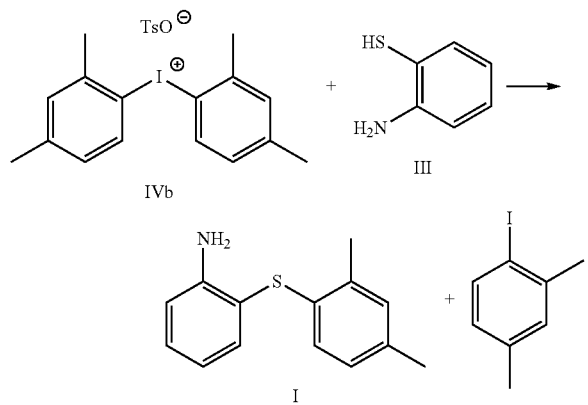

Diaryliodonium salt IVb (0.1 g, 0.19 mmol) and aminothiophenol IIIa (0.0203 ml, 0.19 mmol) are dissolved in 5 ml 1,4-dioxane in autoclave. Trifluoroacetic acid is added (0.056 ml, 0.76 mmol) under stirring. The mixture is stirred at 110° C. till reaction is completed. Then reaction mixture is allowed to cool down to room temperature. DM water is added and the resulting mixture is extracted with diethylether three times. Combined organic layers are washed with DM water and dried over sodium sulfate. Solvents are distilled off and the residue is chromatographed over silica gel to yield compound of formula I.

Example 3: Synthesis of Compound of Formula I from Disulfane IIIb

Example 3a

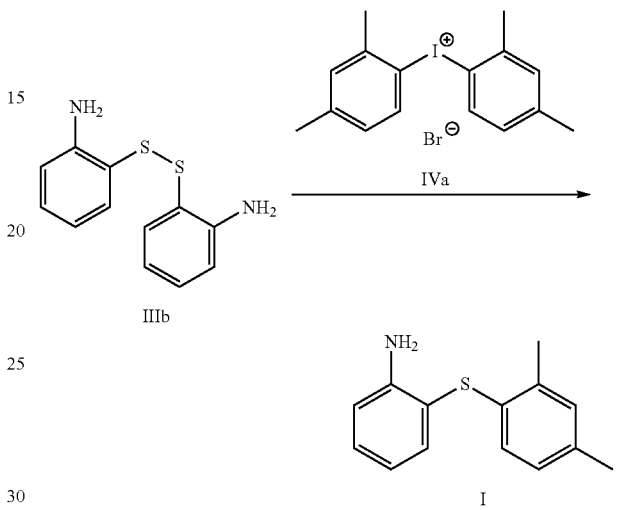

DMSO (1 ml) was added in 5 ml sealed tube containing stirring bar. To this flask, 2,2'-disulfanediyldianiline IIIb (59.6 mg, 0.24 mmol) and bis(2,4-dimethylphenyl) iodonium bromide IVa (200 mg, 0.48 mmol) were added. After this, tert-potassium butoxide (67.3 mg, 0.6 mmol) was added portion wise and resulted reaction mixture was stirred at 40-45° C. for 15 min and then heated at 80° C. The progress of reaction was monitored by TLC. Upon completion of the reaction (3 h), the mixture was cooled to room temperature, poured into water and extracted with 10 mL of ethyl acetate. The combined organic layer was extracted two times with 10 ml brine. First the organic layer was washed with 10 ml 37% HCl twice. 1-iodo-2,4-dimethylbenzene was recovered as a pure product (yield 62%) from the organic phase, whereas the hydrochloric acid of 2-((2,4-dimethylphenyl)thio)aniline was recovered from the aqueous phase. The pH of the aqueous phase is adjusted to 7 with the addition of solid sodium bicarbonate and extracted with ethyl acetate. The organic layer was dried with sodium sulfate and concentrated to give 2-((2,4-dimethylphenyl) thio)aniline as pure product (yield 99%).

Spectroscopic Data of Compound of Formula I $^1$H NMR (500 MHz, CDCl$_3$) δ 7.37-7.35 (d, J=7.8 Hz, 2H), 7.23-7.20 (t, 1H), 7.01 (s, 1H), 6.86-6.85 (d, J=8.2 Hz, 1H), 6.81-6.79 (d, J=8.3 Hz, 1H), 6.77-6.74 (t, 1H), 6.72-6.71 (d, J=7.8 Hz, 1H), 2.39 (s, 3H), 2.27 (s, 3H).

$^{13}$C NMR (126 MHz, CDCl$_3$) δ 148.38, 136.60, 135.79, 135.36, 131.74, 131.20, 130.48, 127.33, 126.60, 118.86, 115.34, 115.13, 20.82, 20.07.

Spectroscopic Data of Recovered 1-iodo-2,4-dimethylbenzene $^1$H NMR (500 MHz, CDCl$_3$) δ 7.68-7.66 (d, J=8.7 Hz, 1H), 7.07 (s, 1H), 6.71-6.69 (d, J=8.1 Hz, 1H), 2.40 (s, 3H), 2.28 (s, 3H).

$^{13}$C NMR (126 MHz, CDCl$_3$) δ 141.00, 138.64, 138.07, 130.76, 128.34, 97.01, 27.92, 20.85.

Example 3b

DMSO (2 ml) was added in 5 ml sealed tube containing stirrer bar. To this flask, 2,2'-disulfanediyldianiline IIIb (119 mg, 0.48 mmol) and bis(2,4-dimethylphenyl) iodonium bromide IVa (400 mg, 0.96 mmol) were added. After this, $^t$BuOK (135 mg, 1.2 mmol) was added portion wise and resulted reaction mixture was stirred at 40-45° C. for 15 min and then heated at 80° C. After 1 h, 2 h and 3 h the reaction mass is checked by TLC in 4/1 Cyclohexane/Ethyl Acetate, following aliquot workup with water and ethyl acetate. The maximum conversion to the target product was 60%.

The reaction mixture was cooled to room temperature, poured into water and extracted with 2×10 mL of ethyl acetate. The combined organic layer were extracted with 2×10 ml Brine. The organic layer was washed with 2×10 ml 37% HCl. 1-iodo-2,4-dimethylbenzene was obtained as a pure product (160 mg), whereas in the aqueous phase there were the hydrochloric acids of 2-((2,4-dimethylphenyl) thio)aniline and 2,2'-disulfanediyldianiline. The pH of the aqueous phase is adjusted to 7 with the addition of solid NaHCO$_3$ and extracted with 2×10 ml ethyl acetate. The organic layer was dried with Na$_2$SO$_4$ and evaporated to give a mixture of 2-((2,4-dimethylphenyl)thio)aniline I and 2,2'-disulfanediyldianiline IIIb (200 mg).

Example 3c

DMF (0.2 ml) was added in 5 ml r.b. flask containing stirrer bar. To this flask, 2,2'-disulfanediyldianiline IIIb (12 mg, 0.048 mmol) and bis(2,4-dimethylphenyl) iodonium bromide IVa (40 mg, 0.096 mmol) were added. After this, $^t$BuOK (13.5 mg, 0.12 mmol) was added portion wise and resulted reaction mixture was stirred at 40-45° C. for 15 min and then heated at 80° C. After 1 h, 2 h and 3 h the reaction mass is checked by TLC in 4/1 Cyclohexane/Ethyl Acetate, following aliquot workup with water and ethyl acetate. The maximum conversion to the target product was 60%.

Example 3d

MeCN (0.2 ml) was added in 5 ml r.b. flask containing stirrer bar. To this flask, 2,2'-disulfanediyldianiline (12 mg, 0.048 mmol) and bis(2,4-dimethylphenyl)iodonium bromide (40 mg, 0.096 mmol) were added. After this, $^t$BuOK (13.5 mg, 0.12 mmol) was added portion wise and resulted reaction mixture was stirred at 40-45° C. for 15 min and then heated at 80° C. The progress of reaction was monitored by TLC. After 1 h, 2 h and 3 h the reaction mass is checked by TLC in 4/1 Cyclohexane/Ethyl Acetate, following aliquot workup with water and ethyl acetate. The maximum conversion to the target product was 40%.

Example 3e

DMSO (2 ml) was added in 5 ml sealed tube containing stirrer bar. To this flask, 2,2'-disulfanediyldianiline (59.6 mg, 0.24 mmol) and bis(2,4-dimethylphenyl)iodonium bromide (200 mg, 0.48 mmol) were added. After this, tBuOK (67.3 mg, 0.6 mmol) was added portion wise and resulted reaction mixture was stirred at 40-45° C. for 15 min and then heated at 80° C. The progress of reaction was monitored by TLC. After 1 h, 2 h and 3 h the reaction mass is checked by TLC in 4/1 Cyclohexane/Ethyl Acetate. ~100 μl are withdrawn from the reaction mass and poured in saturated Brine. The mixture is extracted by ethyl acetate and the organic layer is found to contain a 95:5 mixture of 2-((2,4-dimethylphenyl) thio)aniline and 2,2'-disulfanediyldianiline. The reaction mixture was cooled to room temperature, poured into 10 ml sat. brine and extracted with 2×10 ml of ethyl acetate. The organic layer was washed with 2×10 ml 9N HCl. 1-iodo-2,4-dimethylbenzene was obtained as a pure product (80 mg) after drying with Na$_2$SO$_4$ and evaporation. In the aqueous phase remained the hydrochloric acids of 2-((2,4-dimethylphenyl)thio)aniline and 2,2'-disulfanediyldianiline. The pH of the aqueous phase was adjusted to 7 with the addition of solid NaHCO$_3$ and extracted with 3×10 ml ethyl acetate. The organic layer was dried with Na$_2$SO$_4$ and evaporated to give 97 mg of 2-((2,4-dimethylphenyl)thio)aniline.

Example 3f

DMSO (17 ml) was added in a 3 neck r.b. flask containing stiffing bar. To this flask, 2,2'-disulfanediyldianiline (1.192 g) and bis(2,4-dimethylphenyl)iodonium bromide (4.0 g) were added. $^t$BuOK (1.344 g) was added portion wise at 40-45° C. in a period of 30 min. The mixture then is heated at 80° C. The progress of reaction was monitored by TLC. Upon completion of the reaction (3 h), the mixture was cooled to room temperature, poured into 50 ml brine sat. and extracted with 2×40 mL of ethyl acetate. The organic layers were combined, washed with 3×50 ml brine, dried over sodium sulfate and solvents were distilled off.

The organic layer is concentrated to give an oily mixture. In the oily mixture, hydrogen chloride in diethyl ether (8 ml) is added under stirring with Diethyl ether (20 ml). The 2-((2,4-dimethylphenyl)thio)aniline hydrochloride salt is precipitated, filtered and dried under vacuum (1.72 g).

In the filtrate, there is 1-iodo-2,4-dimethylbenzene and 2-((2,4-dimethylphenyl) thio)aniline as free bases. The filtrate is concentrated to dry and hydrogen chloride in diethyl ether (8 ml) is added in the residue with cyclohexane (50 ml). 2-((2,4-dimethylphenyl)thio)aniline hydrochloride is precipitated. The filtrate is concentrated to give crude 1-iodo-2,4-dimethylbenzene.

Example 3g

For the purpose of the following example, DES-urea, i.e. the ionic compound of choline chloride:urea 1:2, was prepared according to the procedure disclosed in ACIE 2014 53 23 5969.

Des-urea (0.7 ml) was added in a sealed tube containing stirring bar. To this flask, 2,2'-disulfanediyldianiline (29.8 mg) and bis(2,4-dimethylphenyl)iodonium bromide (100 mg) were added. $^t$BuOK (33.65 mg) was added portion wise at 40-45° C. in a period of 5 min. The mixture then is heated at 80° C. The progress of reaction was monitored by TLC. Upon completion of the reaction (3 h), the mixture was cooled to room temperature, poured into saturated brine and extracted with 10 mL of ethyl acetate twice. The organic layers were combined and washed with 10 ml 9N HCl twice, dried over sodium sulfate and solvent was stripped off to provide 26 mg of 1-iodo-2,4-dimethylbenzene as crude oil product. The aqueous phase comprises the hydrochloric acid of 2-((2,4-dimethylphenyl)thio)aniline (HCl salt of compounds of formula I). The pH of the aqueous phase is adjusted to 7 with the addition of solid NaHCO$_3$ and extracted anew with 10 ml ethyl acetate twice. The organic layers were combined, dried with Na$_2$SO$_4$ and evaporated to give the 2-((2,4-dimethylphenyl)thio)aniline as crude oil product (48 mg).

Example 3h

For the purpose of the following example, DES-glycerol, i.e. the ionic compound of choline chloride:glycerol 1:2, was prepared according to the procedure disclosed in ACIE 2014 53 23 5969.

Des-glycerol (0.7 ml) was added in a sealed tube containing stiffing bar. To this flask, 2,2'-disulfanediyldianiline (29.8 mg) and bis(2,4-dimethylphenyl)iodonium bromide (100 mg) were added. $^t$BuOK (33.65 mg) was added portion wise at 40-45° C. in a period of 5 min. The mixture then is heated at 80° C. The progress of the reaction was monitored by TLC. Upon completion of the reaction (3 h), the mixture was cooled to room temperature, poured into sat. brine and extracted with 10 mL of ethyl acetate twice. The organic layers were combined, washed with 10 ml 9N HCl twice, dried over sodium sulfate and solvents were stripped off. 1-iodo-2,4-dimethylbenzene received as crude oil product (27 mg). The aqueous phase comprises the hydrochloric acid of 2-((2,4-dimethylphenyl)thio)aniline aniline (HCl salt of compounds of formula I). The pH of the aqueous phase is adjusted to 7 with the addition of solid NaHCO$_3$ and extracted with 10 ml ethyl acetate twice. The organic layers were combined, dried over Na$_2$SO$_4$ and solvent was evaporated to give the 2-((2,4-dimethylphenyl) thio)aniline as crude oil product (46 mg).

The invention claimed is:

1. A process for the preparation of compound of formula I, comprising subjecting compound of formula III, wherein R is hydrogen or o-aminothiophenolic radical, to reaction with compound of formula IV

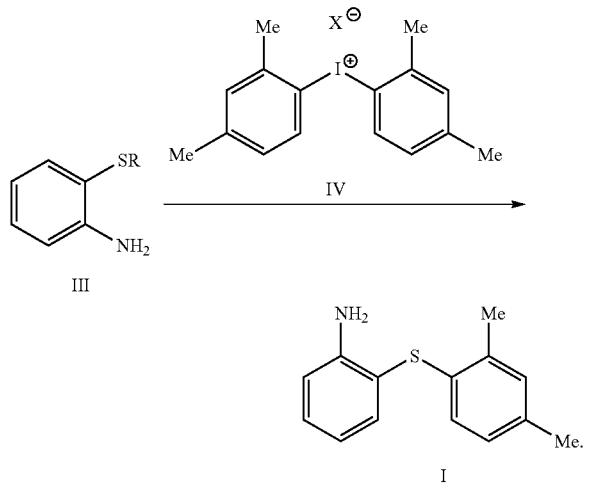

2. A process for the preparation of compound of formula II, comprising the following steps:
   a) subjecting compound of formula III, wherein R is hydrogen or o-aminothiophenolic radical to reaction with compound of formula IV;

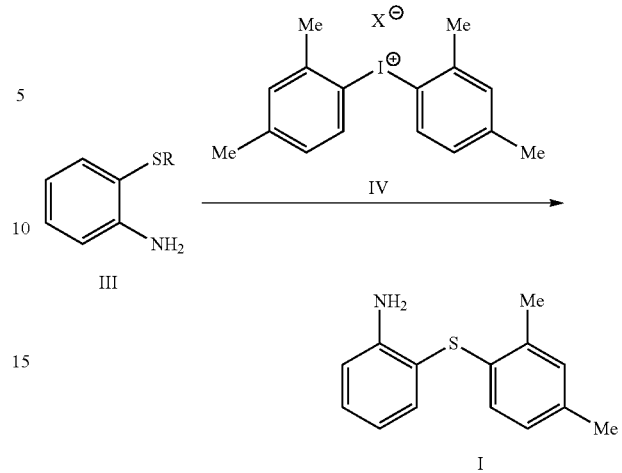

b) converting compound of formula I into compound of formula II

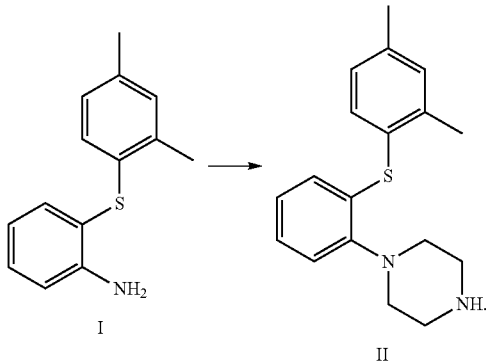

3. A process according to claim 1, wherein anion X is selected from halogen, tosylate, boron tetrafluoride, triflate, perchlorate, trifluoroacetic or acetic anion.

4. A process, according to claim 2, wherein step b is performed by reacting compound of formula I with 2,2'-dichlorodiethylamine.

5. A process according to claim 1, wherein R is hydrogen and compound of formula III is compound of formula IIIa

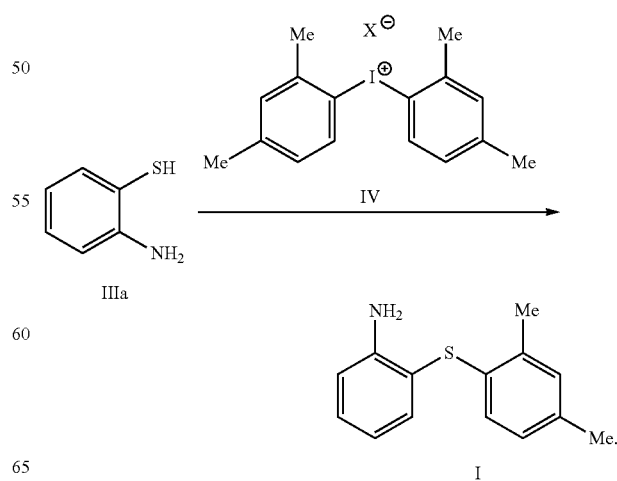

6. A process according to claim 1 wherein R is o-aminothiophenolic radical and compound of formula III is compound of formula IIIb
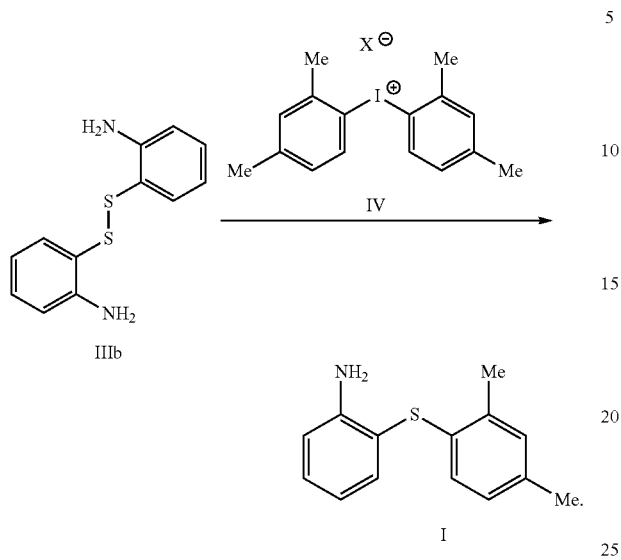
7. A process, according to claim 1, wherein compound of formula V is isolated after the reaction between compounds of formulae III and IV.
* * * * *